US008839793B2

(12) United States Patent
Diaz

(10) Patent No.: US 8,839,793 B2
(45) Date of Patent: Sep. 23, 2014

(54) ADJUSTABLE MANDIBULAR ADVANCEMENT DEVICE

(71) Applicant: Eduardo Diaz, Chula Vista, CA (US)

(72) Inventor: Eduardo Diaz, Chula Vista, CA (US)

(*) Notice: Subject to any disclaimer, the term of this patent is extended or adjusted under 35 U.S.C. 154(b) by 0 days.

(21) Appl. No.: 14/021,160

(22) Filed: Sep. 9, 2013

(65) Prior Publication Data

US 2014/0072927 A1 Mar. 13, 2014

Related U.S. Application Data

(60) Provisional application No. 61/700,274, filed on Sep. 12, 2012.

(51) Int. Cl.
A61F 5/56 (2006.01)
A61C 3/00 (2006.01)
A61C 7/08 (2006.01)
A61C 7/36 (2006.01)

(52) U.S. Cl.
CPC .... A61C 7/36 (2013.01); A61C 7/08 (2013.01)
USPC .............................................. 128/848; 433/6

(58) Field of Classification Search
CPC ...................................................... A61F 5/566
USPC ........... 128/846, 848, 856, 859, 861; 433/6, 2
See application file for complete search history.

(56) References Cited

U.S. PATENT DOCUMENTS

| 4,396,373 | A | * | 8/1983 | Dellinger | ........................ | 433/19 |
|---|---|---|---|---|---|---|
| 6,055,986 | A | | 5/2000 | Meade | | |
| 6,604,527 | B1 | | 8/2003 | Palmisano | | |
| 6,769,910 | B1 | | 8/2004 | Pantino | | |
| 6,983,752 | B2 | | 1/2006 | Garabadian | | |
| 8,136,529 | B2 | | 3/2012 | Kelly | | |
| 2008/0199824 | A1 | | 8/2008 | Hargadon | | |
| 2011/0192404 | A1 | | 8/2011 | Chen | | |
| 2011/0259345 | A1 | | 10/2011 | Cullen | | |
| 2011/0265801 | A1 | | 11/2011 | Cullen | | |
| 2013/0284184 | A1 | * | 10/2013 | Wagner | ......................... | 128/848 |

OTHER PUBLICATIONS

International Search Report and Written Opinion for related PCT application No. PCT/US2013/058691, mailed Dec. 11, 2013, in 10 pages.

* cited by examiner

Primary Examiner — Loan H Thanh
Assistant Examiner — Tarla Patel
(74) Attorney, Agent, or Firm — Procopio, Cory, Hargreaves & Savitch LLP

(57) ABSTRACT

An adjustable mandibular advancement device has an upper plate for covering upper teeth of a human and a lower plate for covering lower teeth of the human. A magnetic closure mechanism is provided in the device in order to hold the upper plate in contact with the lower plate when the device is positioned in a person's mouth. The magnetic closure mechanism includes one or more magnets in the upper plate and one or more magnets in the lower plate. The magnets are positioned so that when the upper plate and lower plate are in contact, the lower plate pulls the person's lower teeth and lower jaw forward and down in order to reduce obstruction of an airway during sleep or physical activity such as sport. An adjustment mechanism between the plates allows the position of the lower plate relative to the upper plate to be adjusted.

6 Claims, 4 Drawing Sheets

ADJUSTABLE MANDIBULAR ADVANCEMENT DEVICE

FIELD OF THE INVENTION

The present invention relates to a mandibular advancement device, and more particularly to an adjustable mandibular advancement device with a magnetic closure mechanism and occlusal adjustment element.

BACKGROUND OF THE INVENTION

It is generally accepted that snoring and obstructive sleep apnea occurs when a human person's tongue fully or partially blocks the airway near the back of the throat, constricting the airway. Lifestyle changes such as exercise and weight loss are helpful to reduce a constricted airway in some people by reducing fat and increasing muscle tone in the throat. However, this approach does not work for all people.

Various devices and approaches to treating these conditions have been proposed. Devices which move the mandible, or lower jaw, forward and down from its habitual position relative to a patient's upper jaw also move the tongue forward and down in the mouth, and are consequently thought to reduce the likelihood of the tongue fully or partially blocking the airway. These devices are known as mandibular advancement devices. Mandibular advancement devices work in part by having a person insert a set of plates which are fitted around the person's teeth—an upper plate fitted around the upper teeth and a lower plate fitted around the lower teeth.

The upper plate and lower plate are then held together via a connecting mechanism, such as a hook, flange or elastic band. The connecting mechanism pulls the lower plate forward and down as described above. However, the connecting mechanism is often irritating, breakable and uncomfortably restrictive, and must be removed or unhooked in order to take out of a person's mouth. Similarly, when inserting the mandibular advancement device, a user must connect the two plates together with the hooks, flanges or bands—a process that can be exceedingly difficult. The connecting mechanism is also located on the buccal surface of the teeth which is immediately adjacent to the soft tissue of the cheek, often causing irritation to the user.

SUMMARY OF THE INVENTION

Embodiments described herein provide an adjustable mandibular advancement device, the mandibular advancement device having an upper plate covering upper teeth of a human and a lower plate covering lower teeth of the human. A magnetic closure mechanism is provided in the device in order to hold the upper plate in contact with the lower plate when the device is positioned in a person's mouth. The magnetic closure mechanism includes one or more magnets in the upper plate and one or more magnets in the lower plate, the magnets in the lower plate having opposite polarities of the magnets in the upper plate such that the magnetic pull of the opposing polarity magnets pulls the upper plate into contact with the lower plate. The magnets are positioned so that when the upper plate and lower plate are in contact, the lower plate pulls the person's lower teeth and lower jaw forward and down in order to reduce obstruction of an airway and prevent snoring and obstructive sleep apnea. The magnetic closure mechanism maintains the device in this position and also provides for unrestricted jaw movement. The mandibular advancement device also includes an adjustable hardware component positioned along an occlusal surface of one of the plates, which allows the upper plate to be adjusted in relation to the lower plate in order to customize the amount of movement provided to the lower teeth and lower jaw.

The mandibular advancement device may be worn while sleeping to reduce the likelihood of the tongue fully or partially blocking the airway. It may also be worn during sports or other physical activities so as to keep the wearer's airway in a more open or efficient condition, so that the wearer takes in more oxygen. This may help to improve physical endurance during sports or other exercise activities.

Other features and advantages of the said invention will become more clear and apparent to those of ordinary skill in the art after reviewing the following detailed description and accompanying drawings.

BRIEF DESCRIPTION OF THE DRAWINGS

The accompanying drawings, which are incorporated in and constitute a part of the specification, illustrate embodiments of the invention and, together with the description, serve to explain the objects, advantages, and principles of the invention. In the drawings.

DETAILED DESCRIPTION OF PREFERRED EMBODIMENTS

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

Embodiments described herein provide for an adjustable mandibular advancement device, the mandibular advancement device having an upper plate covering a portion of upper teeth of a person and a lower plate covering a portion of lower teeth of the person. A magnetic closure mechanism is provided in the device in order to operatively connect the upper plate with the lower plate when the device is positioned in a person's mouth. In addition, an adjustable bite pad with a forward adjustment mechanism may be located in an occlusal area of the upper plate or lower plate to allow a user to adjust the forward positioning of one of the plates relative to the other plate. A plurality of ball clasps may be configured to extend vertically from each of the upper plate and lower plate in order engage an interproximal area of the teeth and hold the upper plate and lower plate in contact with the teeth.

The mandibular advancement device described herein significantly reduces buccal mucosa irritation, tongue irritation, laceration and lip irritation and other discomforts of other mandibular advancement devices by placing adjustable pads in an occlusal area of the teeth as opposed to a buccal or even lingual area of the mouth. The device may be worn while sleeping in order to reduce the likelihood of the tongue fully or partially blocking the airway. It may also be worn during sports or other physical activities so as to keep the wearer's airway in a more open or efficient condition, so that the wearer takes in more oxygen.

Figure 1:
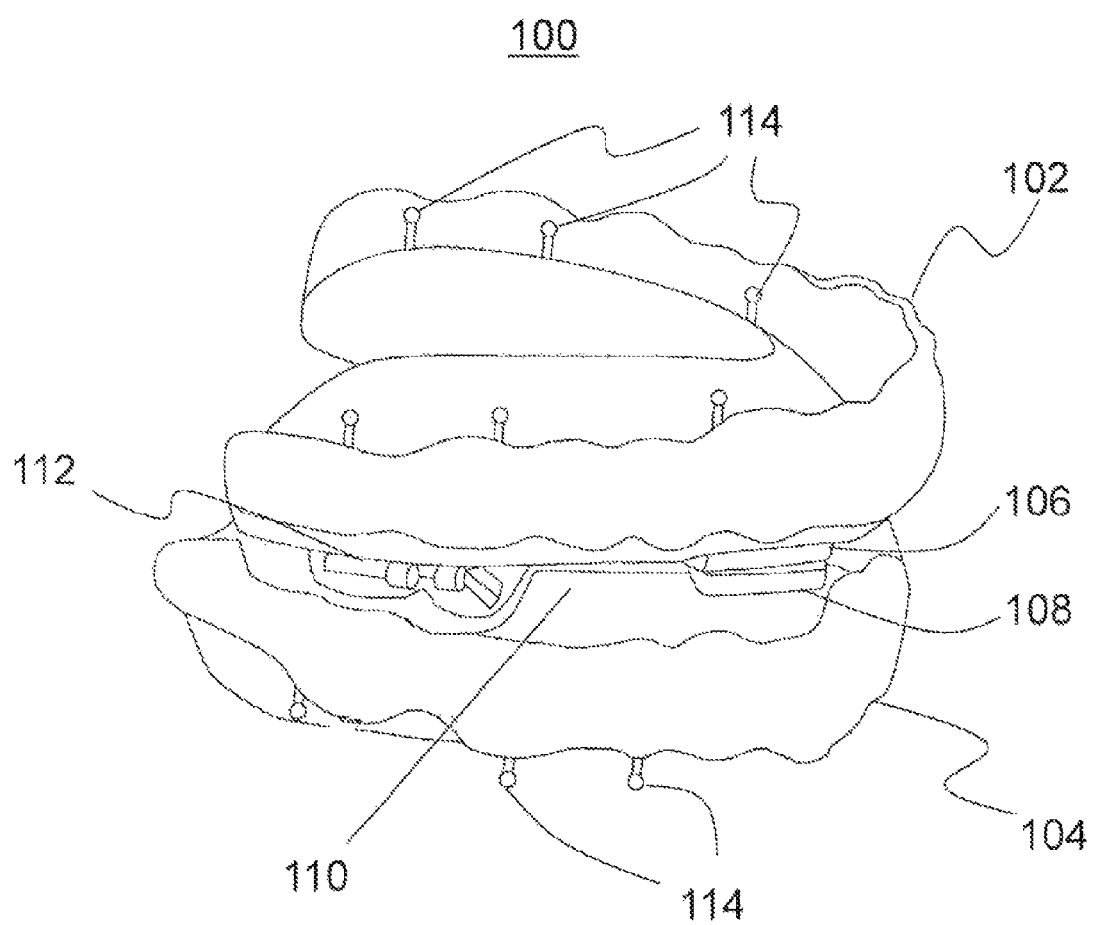
FIG. 1 is a perspective view of a mandibular advancement device illustrating an upper plate, a lower plate, a set of magnets for a magnetic closure mechanism and an adjustable hardware component, according to one embodiment of the invention.
Figure 3:
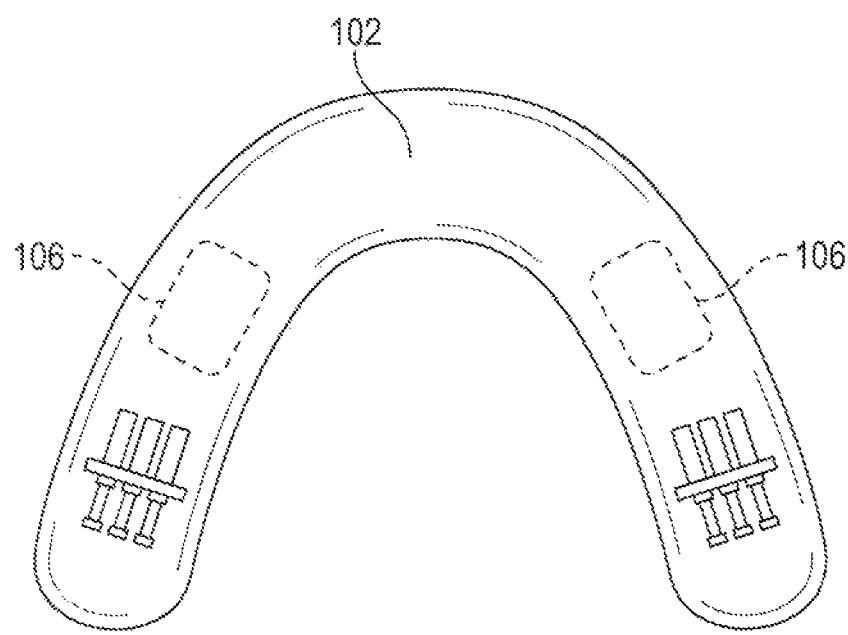
FIG. 3 is a top-down view of the upper plate of the mandibular advancement device of FIG. 1, illustrating a pair of magnets and a pair of hardware adjustment components, according to one embodiment of the invention.
Figure 4:
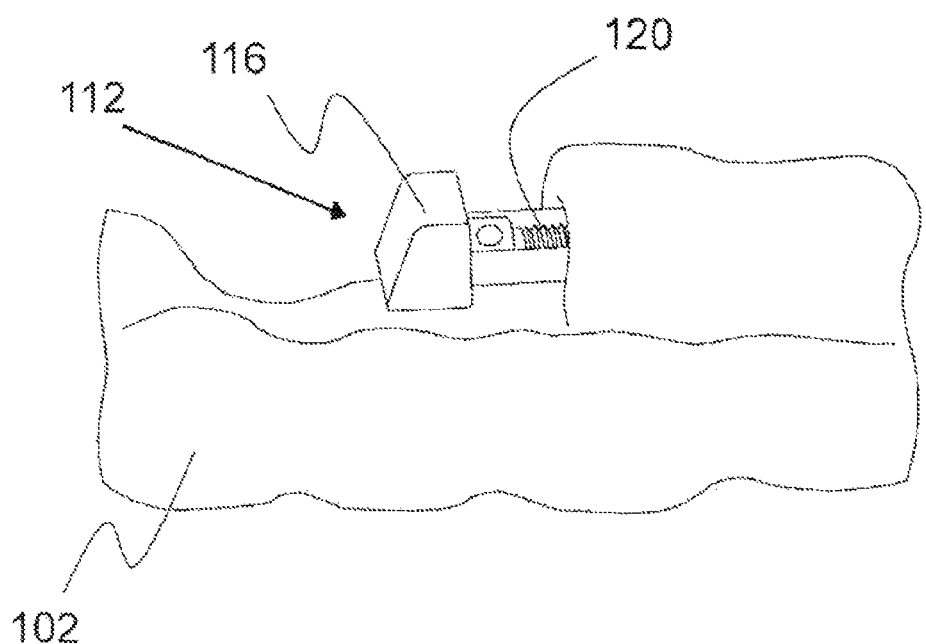
FIG. 4 is a side-angle view of one of the hardware adjustment components of FIG. 3 positioned on an upper side of one side of the upper plate, according to one embodiment of the invention.
Figure 5:
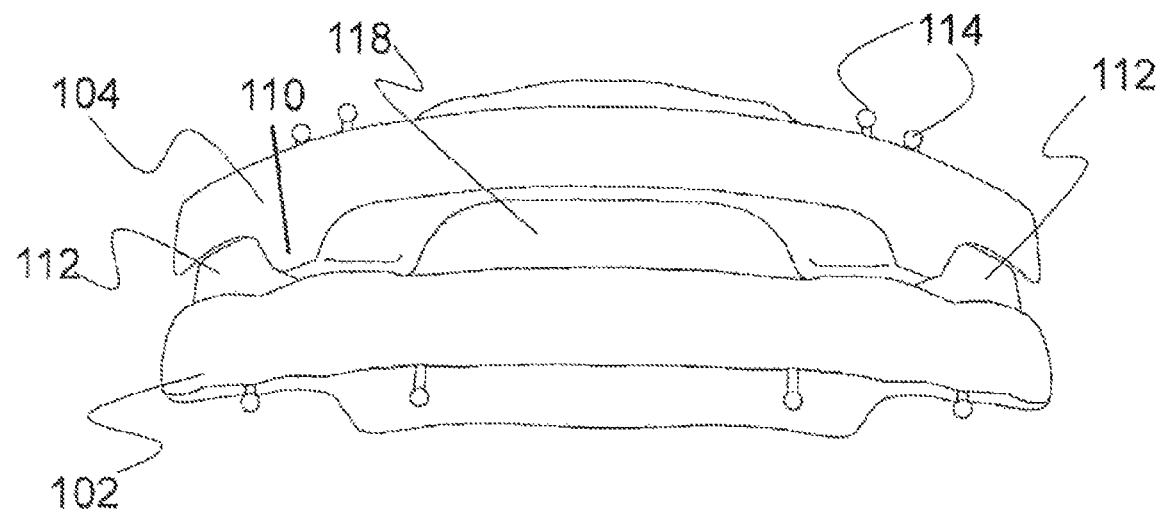
FIG. 5 is a front perspective view of the mandibular advancement device of FIGS. 1 to 4, showing an aperture created at a front side portion of the device when the upper plate is in magnetic contact with the lower plate, according to one embodiment of the invention.
Figure 6:
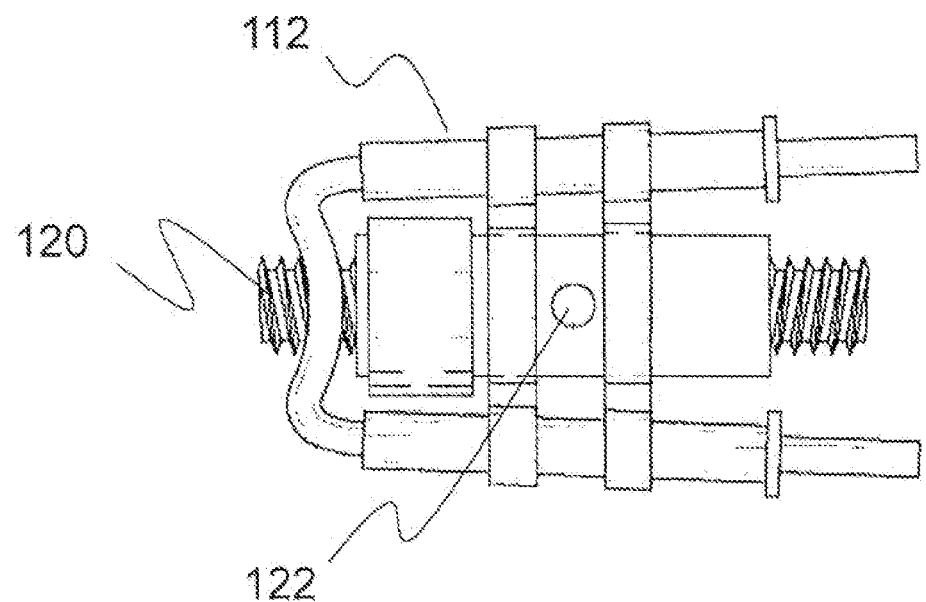
FIG. 6 is a top-down view of the hardware adjustment component of FIG. 4 illustrated separately from the mandibular advancement device, according to one embodiment of the invention.
Figure 7:
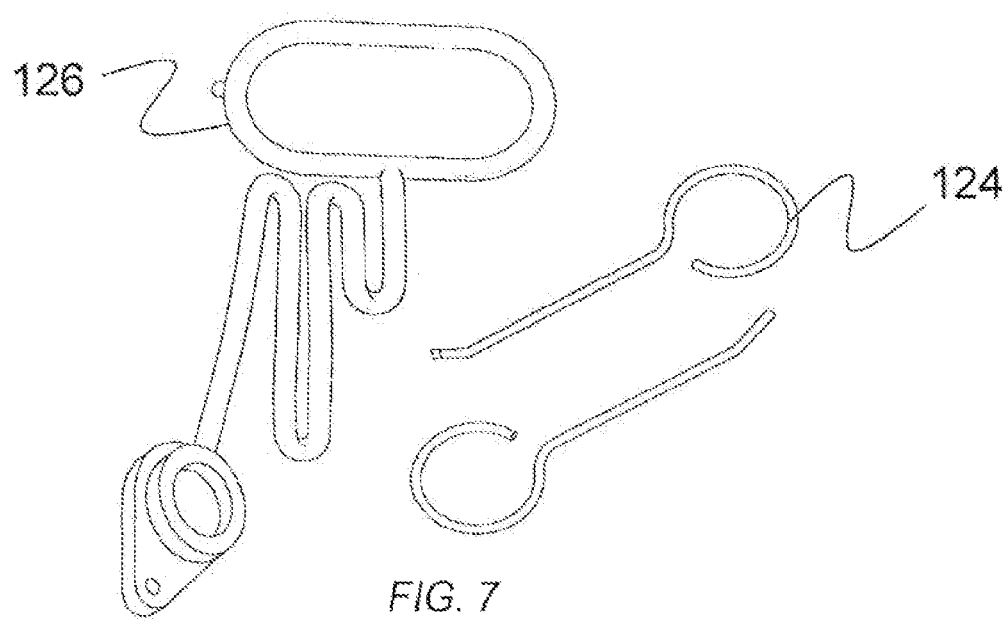
FIG. 7 is an illustration of embodiments of an expansion screw used for adjusting the hardware adjustment component of FIG. 6.

FIGS. 1 to 5 illustrate one embodiment of an adjustable mandibular advancement device 100 while FIG. 6 illustrated an adjustment mechanism 112 of device 100 in more detail, and FIG. 7 illustrates embodiments of an expansion screw which may be used for controlling adjustment. FIGS. 1 and 5 illustrate mandibular advancement device 100 in a closed configuration, as it would look inside of a person's mouth with the mouth closed. The mandibular advancement device 100 includes an upper plate 102 which is configured to fit around a portion of the upper teeth of a user, and a lower plate 104 which is configured to fit around a portion of the lower teeth of the user. The upper plate 102 and lower plate 104 may be made from but not limited to a semi-flexible or flexible material such as a thermoplastic resin, acrylics, composites, and the like. Other types of plastic material suitable for use in the mouth may alternatively be used. The plates may be formed into the specific shape of a user's mouth to provide a comfortable fit.

Figure 2:
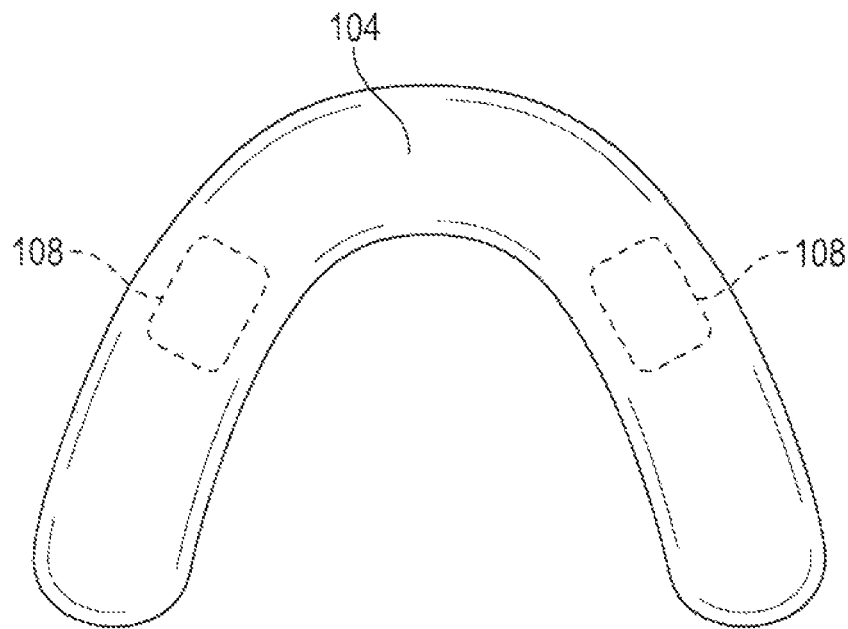
FIG. 2 is a top-down view of the lower plate of the mandibular advancement device of FIG. 1, illustrating a pair of magnets positioned along an upper surface of the lower plate.

A magnetic closure mechanism is provided to operatively connect the upper plate 102 and lower plate 104 into the closed configuration shown in FIGS. 1 and 5. As illustrated in FIGS. 1 to 3, the magnetic closure mechanism in one embodiment comprises an upper magnet 106 on each side of the upper plate 102 and a lower magnet 108 on each side of the lower plate 104, with the lower magnets 108 substantially aligned with the upper magnets in the closed configuration of FIG. 1. The upper magnet 106 and lower magnet 108 are embedded or partially embedded in the respective plate at suitable locations to provide for a desired amount of advancement of a user's lower jaw when wearing the device. As illustrated in FIG. 1, the magnets 106, 108 are located adjacent one another in the closed configuration and are provided with opposite polarities so that they are attracted to one another. In this way, the magnets pull the upper plate 102 and lower plate 104 together so that they are operatively connected. When the plates are operatively connected, the mandibular advancement device effectively pulls the lower jaw forward and down in order to open the user's airway and prevent the user's tongue from obstructing the airway, reducing snoring and sleep apnea.

The magnets 106, 108 are also positioned in an occlusal space (also known as the occlusion) where the upper teeth meet the lower teeth. The magnets 106, 108, along with the mandibular advancement device 100 in general, create a space in the occlusion that keeps the user's jaw slightly opened, reducing the likelihood of airway obstruction. The lower plate 104 may be formed with "occlusal pillars" or raised formations 110 on which magnets 108 are located. As illustrated in FIGS. 1 and 4, the posterior vertical aspect of each pillar 110 is designed to engage with lateral adjustment devices or mechanisms 112 on the upper plate to keep the jaw in the forward position, as described in more detail below.

FIG. 5 depicts the anterior portion of the mandibular advancement device 100 in the closed configuration. When the upper plate 102 and lower plate 104 are operably connected and in the closed condition, as shown here, the opposing portions of the upper and lower plate are designed to provide an aperture 118 at the anterior portion of the device 100 in the front of the wearer's mouth. This aperture creates an anterior opening which allows the tongue to move freely and allows airflow to move freely, increasing the overall comfort to the user and the effectiveness of the device. FIG. 5 also provides an alternate view of the occlusal pillars 110.

FIG. 1 also depicts a forward adjustment mechanism 112, such as an expansion screw, mounted on an occlusal surface of the upper plate facing the posterior aspect of occlusal pillar 110. A similar mechanism 112 is mounted on the opposite side of upper plate 102. Mechanism 112 can be actuated to adjust forward the pillar 110 and move the mandible of the user forward in small increments in order to achieve an ideal position for the device to be effective, as described in more detail below.

In one embodiment, a plurality of ball clasps 114 are positioned at various locations along the upper plate 102 and lower plate 104, where they extend vertically away from the plates into the area where the plates fit into the teeth. The ball clasps 114 are used to engage an interproximal area of the teeth (a space between one tooth and an adjacent tooth) and help to retain the upper plate and lower plate on their respective upper teeth and lower teeth.

Magnetic Closure Mechanism

The magnets 106, 108 are positioned so that when the upper plate and lower plate are in contact, the lower plate pulls the person's lower teeth and lower jaw forward and down in order to reduce obstruction of an airway and prevent snoring and obstructive sleep apnea. The magnetic closure mechanism provides a user with advancement of the lower jaw when the upper plate and lower plate are operatively connected, but also provides for freedom of movement of the jaw by exerting a minimal force to overcome the magnetic force and operatively disconnect the upper plate and lower plate. A user is then free to open their mouth to speak, get a drink and otherwise move the jaw in any direction temporarily before closing the mouth again to operatively connect the upper and lower plates. The magnetic closure mechanism is also located in an occlusal area where the upper teeth contact the lower teeth, which does not irritate a user, unlike a hook, flange or elastic band running along a buccal surface of the outside of the teeth as in previous such devices.

FIG. 2 is a top plan view of the lower plate 104 of the mandibular advancement device, depicting the two lower magnets 108 partially embedded in the body of the lower plate and positioned on either side of the lower plate 104. FIG. 3 illustrates a bottom plan view of the upper plate 102 depicting two upper magnets 106 partially embedded in the body of the upper plate and positioned similarly to the lower magnets 108 in FIG. 2, such that the respective upper and lower magnets are adjacent to one another when the mandibular advancement device is being worn and the mouth is in a closed position. As seen in FIGS. 2 and 3, the magnets 106, 108 are oriented at an angle to follow the curve or angle of the side of the plate in which they are located, i.e. so that they follow the curvature of the mandible.

The magnets may be configured in almost any shape that may be convenient for the design of the upper and lower plates, such as the rectangular-shaped magnets shown herein. In other embodiments, the magnets may be curved or arcuate in shape, or may be disc-shaped, and one, two, or more magnets may be provided on each side of the respective plate.

In one embodiment, the magnets may be neodymium magnets with a strength of N52. A rectangular-shaped magnet of N52 strength can be utilized in any size configuration, for example, with dimensions of at least approximately 3/8" Long×at least approximately 3/16" Wide×at least approximately 1/16" Thick. For a round magnet, the dimensions can be utilized in any size configuration, for example, with dimensions of at least approximately 5/16" in diameter and at least approximately 1/16" thick, again with a strength of N52 (residual flux density), a (Br) of 14.5-14.8 Kg in coercive force (Hc), greater than 11.2 KOe of intrinsic coercive force (Hci), greater than 11 KOe of maximum energy product (BH) max, and 49.5-52 MGOe.

In one embodiment, the magnets are positioned near a front section of the device, in the premolar, canine area, but before the general curvature of the anterior portion of the teeth, as this will provide for a sufficient opening in the anterior portion of the mouth to keep the airway open. The magnets may be covered by the same material as the upper and lower plates, such as a thermoplastic resin, acrylic, etc., as this will prevent any risk of corrosion of the magnets.

In one embodiment, additional magnets may be positioned in the upper and lower plates in order to provide for a stronger operative connection or to provide for a more distinct pull. In another alternative embodiment, one or more magnets may be located to the rear of the position shown in FIGS. 1 to 3, to leave forward portions of the plates unattached.

Occlusal Adjustment Element

FIG. 4 illustrates a side perspective view of one embodiment of the occlusal adjustment mechanism 112. A similar mechanism may be provided on the opposite side of the upper plate 102. The mechanism 112 has a lateral actuation head 116 designed to engage the adjacent occlusal pillar 110 on the lower plate 104 in order to adjust an offset between the upper and lower plates. In one embodiment, the occlusal adjustment mechanism 112 is positioned on an occlusal surface of the upper plate 102. There can also be an occlusal adjustment mechanism 112 positioned on the occlusal surface of the lower plate 104. The occlusal adjustment mechanism 112 may be substantially covered by the material used to form the upper plate 102, and provide only a small opening where a lateral actuation head 116 extends outward to engage an opposing portion of the respective occlusal pillar of the lower plate (see FIGS. 4 and 5) and adjust the positioning of the mandibular advancement device. In FIG. 4, the occlusal adjustment mechanism is an expansion screw 120 which may be manually actuated to extend the occlusal actuation head 116 forward and away from a fixed end of the occlusal adjustment mechanism 112. The occlusal actuation element or head 116 may be made of but not limited to metal, acrylic or thermoplastic resin like the other portions of the upper plate.

In one embodiment, the user may be able to adjust the occlusal adjustment element to move approximately 10 millimeters (mm), which helps the user adjust the fit of the mandibular advancement device so that it provides a sufficient opening of the airway and clearance of the tongue at the back of the airway. As shown in FIG. 1, if the occlusal adjustment mechanism actuates in the anterior direction, it will impact the lower plate 104 and push the lower plate 104 in the anterior direction as well, thereby pushing the lower jaw further forward and down.

The occlusal adjustment elements are used to adjust the mandible of the user to achieve an ideal mandible position. The starting point of any bite, or mandible position of the user, is determined by a bite registration technique for mandibular advancement, examples of which include The George Gauge™, The Andra Gauge™, and Sibilant Phoneme Registration.

FIG. 6 illustrates one embodiment of a forward adjustment mechanism 112 having an expansion screw 120. Actuation head 116 (not illustrated) is attached to an end of screw 116. The expansion screw may be actuated at an actuation opening 122 where an actuation tool 124 shown in FIG. 7 can be inserted in order to turn the expansion screw 120 in one direction or another depending on the type of adjustment desired, and thus move a suitable actuation element 116 secured to a distal end of the screw. Alternatively, the opposite end of the screw 120 may engage in a threaded bore in a portion of the lower plate to move the lower plate relative to the upper plate. An alternative adjustment element tool 126 may also be used for adjustments. This adjustment element tool 126 is used to move the screw on the adjustment element. The adjustment element tool 124 or 126 is held from the round end and the tip of the tool at the other end is inserted into the screw hole or actuation opening 122 to move the screw forward or backwards.

The adjustment mechanism in this embodiment is provided between opposing occlusal surfaces of the upper and lower plates, and does not extend out from the buccal surfaces where it could irritate the adjacent soft tissue of the wearer's cheek, unlike prior art devices.

Ball Clasps

The ball clasps 114 are used to retain the upper plate and lower plate against the teeth when the device is being worn by the user. The ball clasps, depicted in FIG. 1 and FIG. 4, are spaced along peripheral edges of the respective upper plate and lower plate at positions where they engage an interproximal area of the teeth. As shown in FIGS. 1 and 4, they may be rounded on their tips to minimize discomfort for the user. In one embodiment, the ball clasps 114 are made of surgical-grade steel and extend vertically from wires embedded within the upper or lower plate to provide strength.

In one embodiment, four ball clasps are positioned along the device—two in a posterior area of the mouth where the molar teeth fit into the plates, and two in the anterior area.

In one embodiment, the mandibular advancement device may be formed using a vacuum-form process with a more flexible material which provides a highly accurate and strong fit of the upper and lower plates to the user's teeth, to the point where the ball clasps are not needed.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A mandibular advancement device, comprising:
a first plate and a second plate, the plates comprising an upper plate configured for fitting around a portion of the upper teeth and a lower plate configured for fitting around a portion of the lower teeth of a user;
the upper plate having at least one upper magnet of a first polarity at least partially embedded therein;
the lower plate having at least one lower magnet of a second polarity at least partially embedded therein;
wherein the upper plate and lower plate are operatively connected by magnetic attraction between the upper magnet and lower magnet when the user has the upper plate fitted around the portion of the upper teeth and the lower plate fitted around the portion of the lower teeth;
wherein the upper and lower plates each have opposite side portions configured for fitting over the teeth on opposite sides of the user's upper and lower jaw, respectively, the opposite side portions having rear ends, and an anterior portion extending between the side portions configured for engaging over the teeth at the front of the wearer's jaw, at least a first upper magnet and a second upper magnet are located in opposite side portions of the upper plate and at least a first lower magnet and a second lower magnet are located in opposite side portions of the lower plate, wherein the upper plate and the lower plate are operatively connected by magnetic attraction between the first upper magnet and first lower magnet and the second upper magnet and second lower magnet on the opposite side portions of the plates when the upper and lower plates are fitted around a portion of the upper and lower teeth, respectively, of the user; and
each side portion of the first plate has an occlusal pillar in which a respective magnet is located; wherein a respective adjustment mechanism is located in an occlusal surface of each side portion of the second plate adjacent a respective occlusal pillar of the first plate when the device is worn by a user, each adjustment mechanism having a movable actuation element configured to engage an opposing portion of the respective occlusal pillar and adjust an offset between the upper and lower plate when the adjustment mechanism is actuated.

2. The mandibular advancement device of claim 1, wherein the upper plate and lower plate form an aperture at an anterior portion of the upper teeth and lower teeth when the upper plate and lower plate are operatively connected.

3. The mandibular advancement device of claim 1, wherein the upper plate and lower plate are formed from a rigid material, a flexible material or a semi-flexible material.

4. The mandibular advancement device of claim 1, further comprising a plurality of ball clasps in the upper plate and lower plate which extend vertically away from an occlusal surface of the respective plate and are configured to engage respective interproximal areas of the upper teeth and lower teeth of the user.

5. The mandibular advancement device of claim 1, wherein the magnets are spaced from the rear ends of the respective plate side portions and are located closer to the anterior portion of the respective plate than said rear ends.

6. The mandibular advancement device of claim 1, wherein the first plate is the lower plate and the second plate is the upper plate, and the occlusal pillars of the lower plate are located forward of the respective adjustment mechanism of the upper plate when the upper and lower plates are located around portions of the user's upper and lower teeth, respectively.

* * * * *